(12) United States Patent
Wang et al.

(10) Patent No.: US 11,719,622 B2
(45) Date of Patent: Aug. 8, 2023

(54) APPARATUS FOR QUICKLY DISPLAYING CORONAVIRUS TEST RESULT

(71) Applicant: ARION BIO, INC., Dublin, CA (US)

(72) Inventors: Yongbo Wang, Dublin, CA (US); Honglin Liu, Dublin, CA (US)

( * ) Notice: Subject to any disclaimer, the term of this patent is extended or adjusted under 35 U.S.C. 154(b) by 309 days.

(21) Appl. No.: 17/069,808

(22) Filed: Oct. 13, 2020

(65) Prior Publication Data

US 2022/0113245 A1   Apr. 14, 2022

(51) Int. Cl.
*G01N 21/01* (2006.01)
*G01N 21/64* (2006.01)

(52) U.S. Cl.
CPC ......... *G01N 21/01* (2013.01); *G01N 21/6428* (2013.01); *G01N 2021/0112* (2013.01); *G01N 2201/0221* (2013.01); *G01N 2201/0626* (2013.01)

(58) Field of Classification Search
CPC ............... G01N 21/01; G01N 21/6428; G01N 2201/0221; G01N 2201/0626; G01N 2021/0112; G01N 33/582; G01N 2800/26; G16H 40/67; G16H 20/10; G16H 10/60
USPC .......................... 356/300–326, 246, 432–440
See application file for complete search history.

(56) References Cited

U.S. PATENT DOCUMENTS

2019/0381499 A1* 12/2019 Johnson ........... A61B 5/150755

FOREIGN PATENT DOCUMENTS

CN       107102144 A   *   8/2017
CN       111435136 A   *   7/2020

* cited by examiner

*Primary Examiner* — Hoa Q Pham
(74) *Attorney, Agent, or Firm* — Dahyee Law Group; Leon E. Jew; Lin Kong

(57) ABSTRACT

The present invention teaches an apparatus for consistent and accurate on-site readings of fluorescence signals of coronavirus test result, with which a user directly reads a fluorescent light qualitatively instead of using electronic sensors. The fluorescent light is excited from a fluorescent source in a site of interest in a target assay. The device comprises a light source for generating an excitation light for exciting the fluorescent source of the target assay to generate a fluorescent light, a component for accurately transmitting the excitation light and the fluorescent light with less noise or reflection, a component for consistent detecting of the fluorescent source by bare eyes with minimal health risks, and a user control system that requires minimal training.

1 Claim, 6 Drawing Sheets

APPARATUS FOR QUICKLY DISPLAYING CORONAVIRUS TEST RESULT

FIELD OF THE INVENTION

The present invention generally relates to the technology of reading fluorescent signals for coronavirus test result. More particularly, the invention is related to an apparatus for quickly displaying coronavirus test result by providing consistent and accurate on-site readings of fluorescence signals, with which an ordinary person can operate a coronavirus test at home without need a medical professional's assistance.

BACKGROUND OF THE INVENTION

Fluorescence and Colloidal Gold Conjugate are two main signal rendering methods in the diagnostic fields. Fluorescent immunoassay functions by marking the target analyte with a specially designed antibody, which emits light after exposure to UV light sources.

While the fluorescent method is generally more sensitive than the Colloidadel Gold method, tests targeting OTC or Point of Care market use mostly Colloidal Gold method. The main reason is that current Colloidal Gold immunoassay design performs better in terms of usability and consistency in non-professionals. The colloidal gold allows direct coloration on the test strips, where no additional equipment or training is needed; meanwhile, using fluorescent immunoassay requires a specialized reader that shines UV light and reads the response signals.

The readers in the market right now are usually designed for high-throughput laboratories, which means they are capable for automated high-volume testing but they are too expensive and they require much more sophisticated training for the public. This is a significant drawback as having the sensitivity advantage not available to the public significantly reduces chances of early diagnosis.

In the context of COVID-19 pandemic, what is needed is an apparatus for consistent and accurate on-site readings of fluorescence signals in a coronavirus test, with which an ordinary person can operate a coronavirus test at home or work place without need of a medical professional's assistance.

SUMMARY OF THE INVENTION

The present invention discloses an apparatus for quickly displaying coronavirus test result by providing consistent and accurate on-site readings of fluorescence signals, with which an ordinary person can operate a coronavirus test at home without need a medical professional's assistance.

In one preferred embodiment, the present invention teaches an apparatus for consistent and accurate on-site readings of fluorescence signals, wherein a user directly reads a fluorescent light qualitatively instead of using electronic sensors. The fluorescent light is excited from a fluorescent source in a site of interest of a target assay. The apparatus includes a light source for generate an excitation light for exciting the fluorescent source of the assay to generate a fluorescent light, a component for accurately transmitting the excitation light and the fluorescent light with less noise or reflection, a component for consistent detecting of the fluorescent source by bare eyes with minimal health risks, and a user control system that requires minimal training.

In another preferred embodiment of the present invention, the apparatus further includes a semi-closed chamber which is used as a backbone to contain all other components. Preferably, the chamber is made of impermeable materials that can shield the light transmission channels from suspending particles and environmental light noises.

In another preferred embodiment of the present invention, the apparatus backbone is made of a designated color to better contrast the signal fluorescent light.

In another preferred embodiment of the present invention, the apparatus contains a docking space, through which the apparatus is designed to a shape such that the docking space closely fits and stationizes the assay to be analyzed. The apparatus further includes a plurality of anchor points that reduce spatial variability of all other components, consequently limiting the user's variability in terms of shaking or wrong direction during reading process.

In another preferred embodiment of the present invention, wherein the chamber is made of PVC.

In another preferred embodiment of the present invention, the light source is generated by using two UV-C LED lights, each of the UV-C LED lights having frequency approximately 365 nm and power approximately 0.5 Watts.

In another preferred embodiment of the present invention, the apparatus further includes a viewing window and a plurality of spectral filtrations which is applied either to the viewing window or the light source in order to avoid coincidence of the fluorescent light and the excitation light and prevent the user's body from exposure to the lights.

In another preferred embodiment of the present invention, the excitation light source is arranged to be not directly exposed or imposing any strong reflection into the user's eyes for safety and sensitivity concerns.

In another preferred embodiment of the present invention, the excitation light sources are installed in an arrangement such that the excitation light primarily illuminates the site of interest of the assay to be analyzed.

In another preferred embodiment of the present invention, the site of interest of the assay to be analyzed and the excitation light source is placed at a 45 degrees angle and 10 mm distance, which results in least deflection.

In another preferred embodiment, the present invention teaches a method for operating the apparatus for assist analysis of the fluorescence source of the assay to be analyzed and the apparatus further includes a program, size and a plurality of specifications of the excitation light source, a docking space and a power button. The method includes the following steps: (1) making sure the program, size and the plurality of specifications of the excitation light source matching the assay to be analyzed; (2) inserting the assay to be analyzed into the docking space; (3) turning on the apparatus by pressing the power button; (4) emitting the excitation light to shine on the site of interest of the assay to be analyzed and excite the fluorescent source within the assay to be analyzed, which then emits fluorescent light as responses; and (5) observing the site of interest by the user according to the instruction for use of the assay to be analyzed.

The advantages of this invention are numerous. First, the invention is economic and easy to use, which allows for the public to afford and operate fluorescent-based tests at frequent interval without professional guidance. This allows rapid fluorescent testing at small or medium events like sport festival, which was not feasible priorly due to the complexity and cost of laboratory-level fluorescence readers. As mentioned in the background of the invention, fluorescence-based tests are generally more sensitive than current OTC methods. This difference in sensitivity, when amplified by mass implementations, can save a significant number of people. Second, the invention enables consistent and safe reading of fluorescent signals comparing to other lower-priced on-site fluorescence reading methods, such as hand-held ultraviolet lights. This is an important improvement as the readability of fluorescence signals are sensitive to environments and users' habits, which could lead to false readings.

BRIEF DESCRIPTION OF DRAWINGS AND TABLES

DETAILED DESCRIPTION OF THE INVENTION

Figure 1:
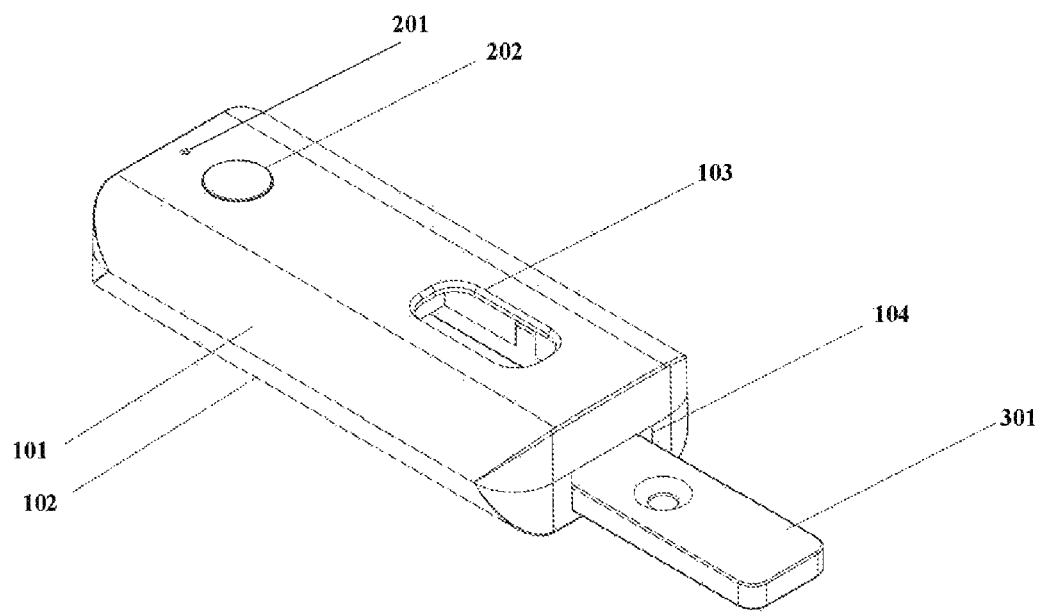
FIG. 1 is a schematic representation of a perspective view of the casing of the apparatus according to the present invention, with a sliding member for holding assay holder 301.

The present invention discloses an apparatus for consistent and accurate on-site readings of fluorescence signals, wherein a user directly reads a fluorescent light qualitatively instead of using electronic sensors. While the present invention may be embodied in many different formulas for the purpose of promoting an understanding of the principles of the invention, reference will be made to the embodiments illustrated in the drawings, tables and specific language will be used to describe the same. It will nevertheless be understood that no limitation or restriction of the scope of the invention is thereby intended. Any alterations and further implementations of the principles of the invention as described herein are contemplated as would normally occur to one skilled in the art to which the invention relates.

Terms and Definitions

In this invention, a user is the operator who physically handles the apparatus, and a subject is the human or animal whose specimen were drawn.

An assay refers to or means a test mechanism that analyzes clinical specimens and inform about specimen composition, and an analyte refers to a substance of interest that could be found in specimen.

A fluorescent source refers to or means a fluorophore, or a biochemical compound that can re-emit light upon light excitation. For example, a fluorescent source could refer to Green Fluorescent Proteins or fluorescent microspheres such as Polystyrene nanoparticles.

A site of interest refers to or means a place, an area, a component, a channel, or a side of the assay where results are delivered, or places where reaction happens most intensively. For example, it could be the antibody-labeled band for immunoassays, where fluorescence signal at the band informs about the detectable presence of the target analyte; or, it could refer to the reaction chamber for microfluidics.

A light source for generating an excitation light, or excitation light source means an apparatus or mechanism that is capable of emitting light of frequencies within the significant adsorption spectrum of the fluorescent source at reasonable intensity. For an example, a 0.5 W light emitting diode of frequency 365 nm is qualified as an excitation light source, as the light that it emits can induce fluorescence of polystyrene fluorescent microsphere continuously, and the fluorescent light emitted is at the intensity visible to average users.

In a typical configuration according to the preferred embodiment as illustrated in FIGS. 1-12, the invention teaches an apparatus for quickly displaying coronavirus test result by providing consistent and accurate on-site readings of fluorescence signals, with which an ordinary person can operate a coronavirus test at home without need a medical professional's assistance. Using the apparatus, a user directly reads a fluorescent light qualitatively without the necessity of electronic sensors.

Figure 2:
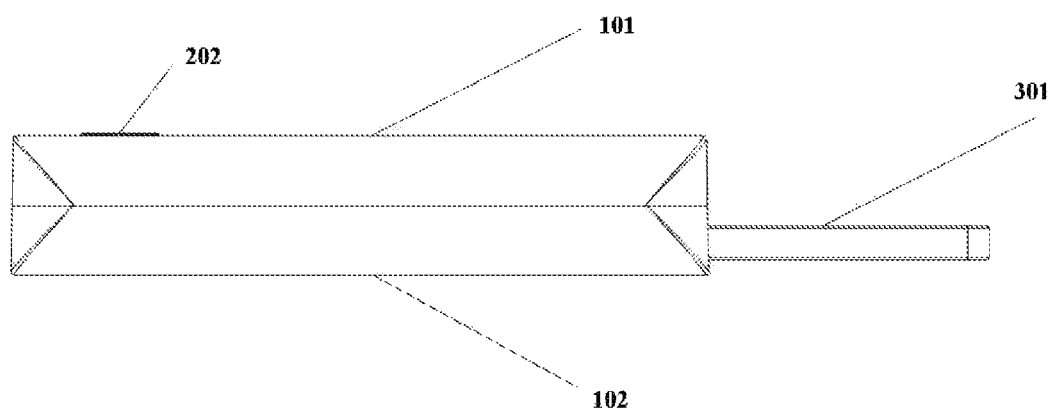
FIG. 2 is a schematic representation of a lateral view of the apparatus of FIG. 1, with the assay holder 301 inserted.
Figure 3:
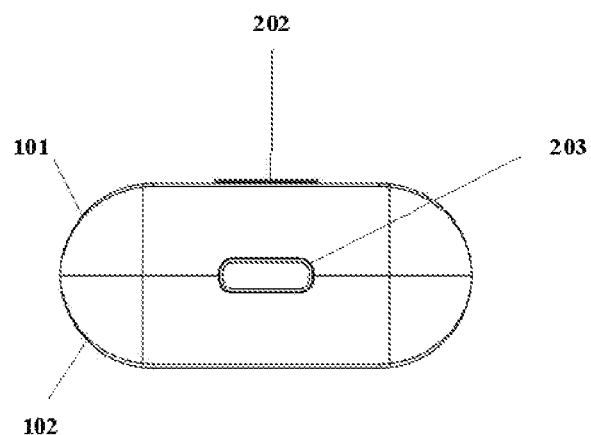
FIG. 3 is a schematic representation of a posterior view of the apparatus of FIG. 1.
Figure 4:
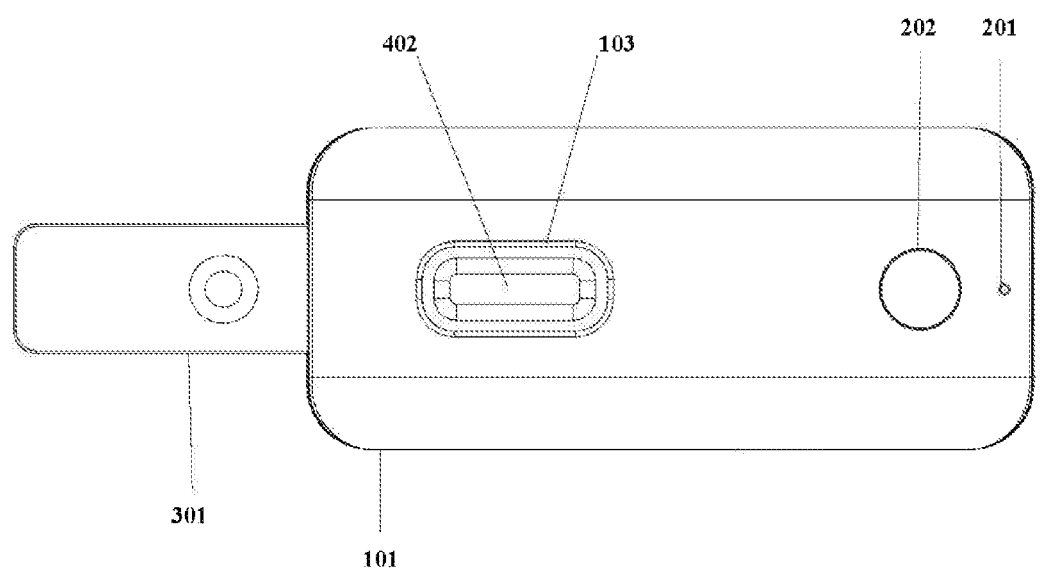
FIG. 4 is a schematic representation of a top view of the apparatus of FIG. 1, with the assay holder 301 inserted.
Figure 5:
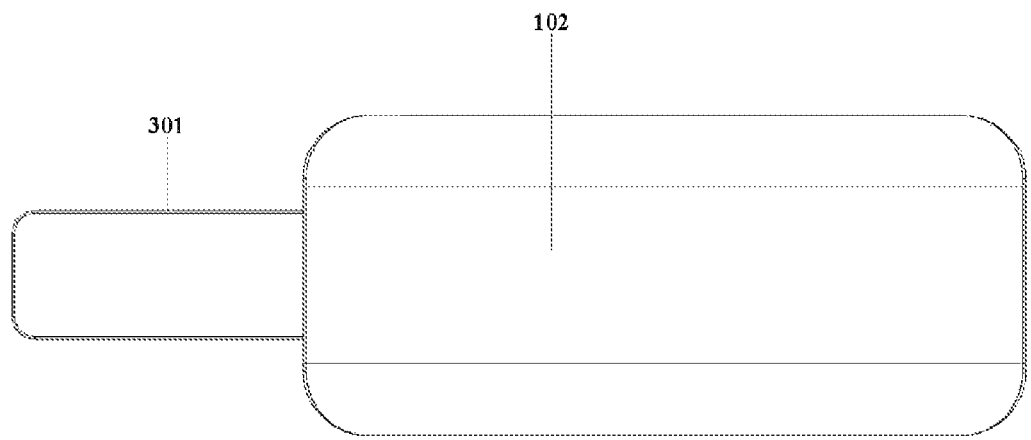
FIG. 5 is a schematic representation of a bottom view of the apparatus of FIG. 1, with the assay holder 301 inserted.
Figure 6:
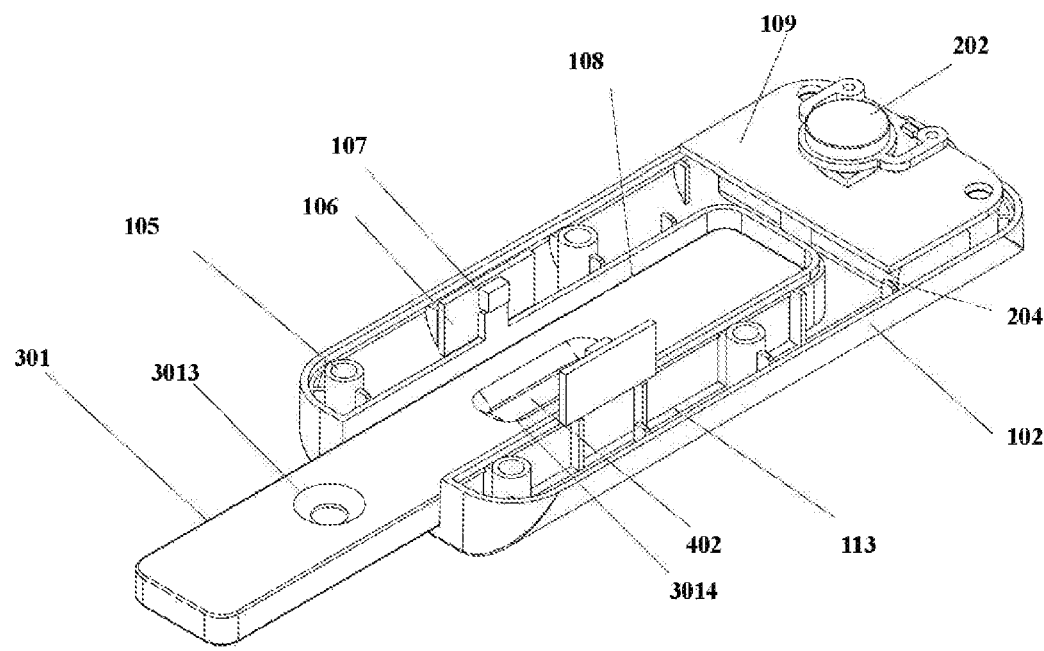
FIG. 6 is a schematic representation of a perspective section view of the apparatus of FIG. 1, with the assay holder 301 inserted but the upper casing 101 removed.
Figure 7:
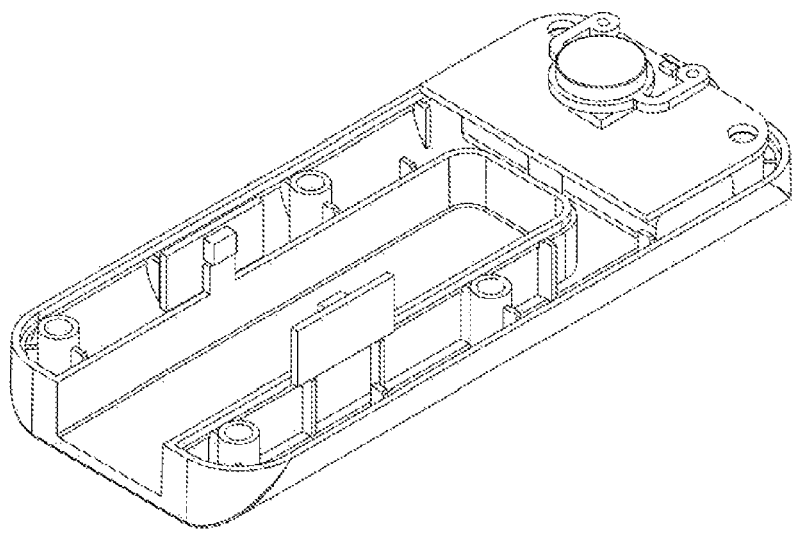
FIG. 7 is a schematic representation of a perspective section view of the apparatus of FIG. 1, without showing the upper casing 101 and the assay holder 301.
Figure 8:
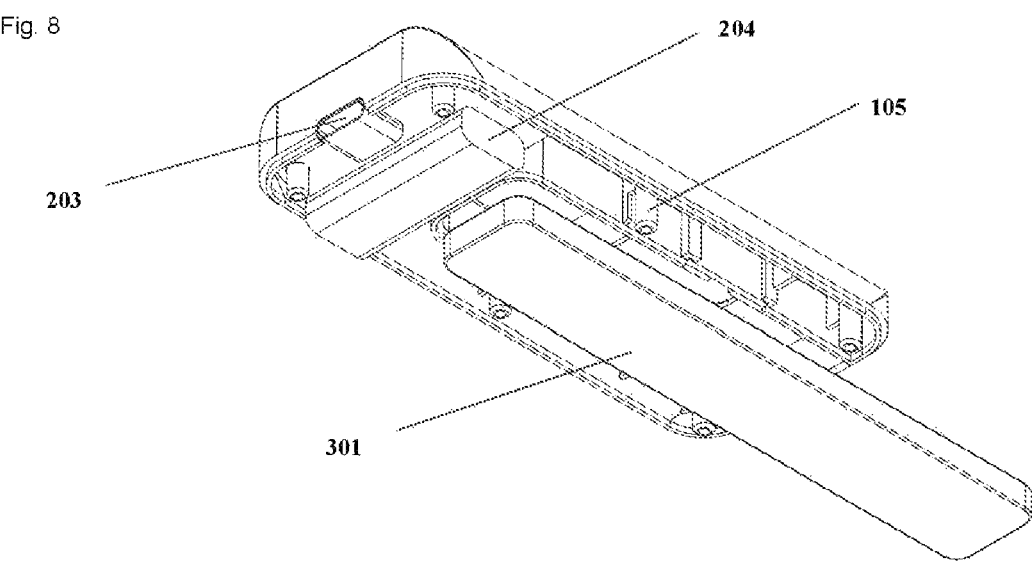
FIG. 8 is a schematic representation of a perspective section view from the bottom of the apparatus of FIG. 1, showing the assay holder 301 inserted, but not showing the lower casing 102.
Figure 9:
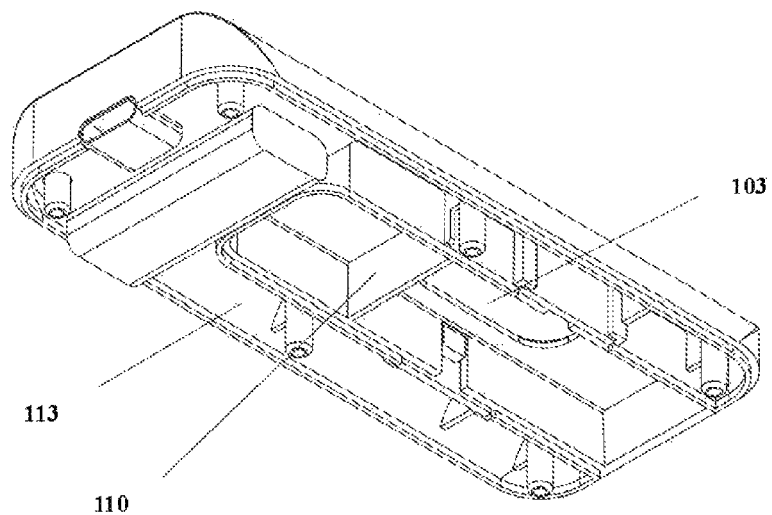
FIG. 9 is a schematic representation of a perspective section view from the bottom of the apparatus of FIG. 1, without showing the lower casing 102.
Figure 10:
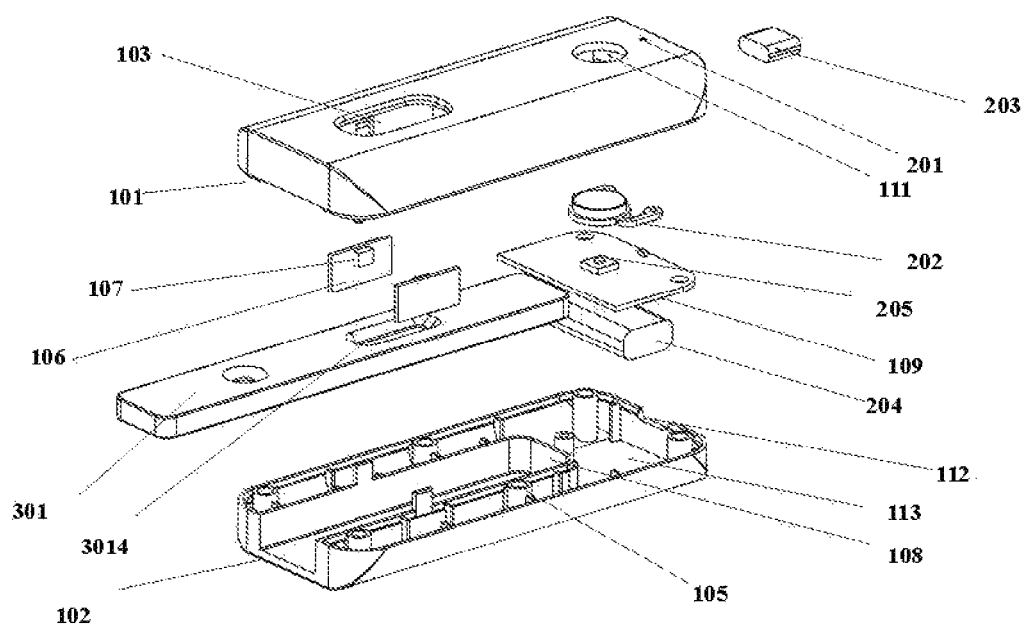
FIG. 10 illustrates an exploded view of the apparatus assembly of the preferred embodiment, including the assay holder 301 as a reference.
Figure 11:
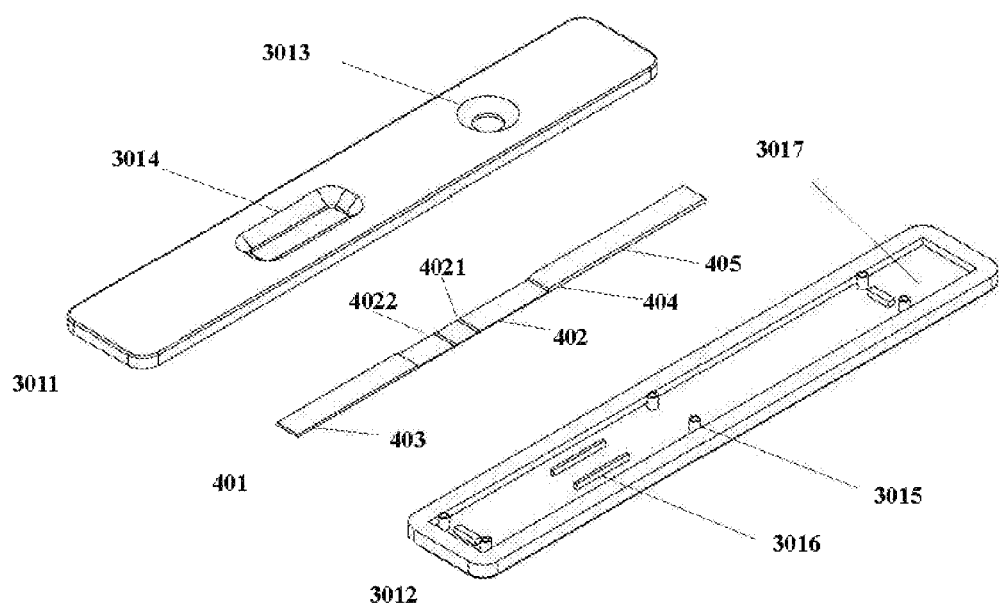
FIG. 11 illustrates an exploded view of the assembly and sub-components of the assay holder 301 and the assay to be analyzed 401.
Figure 12:
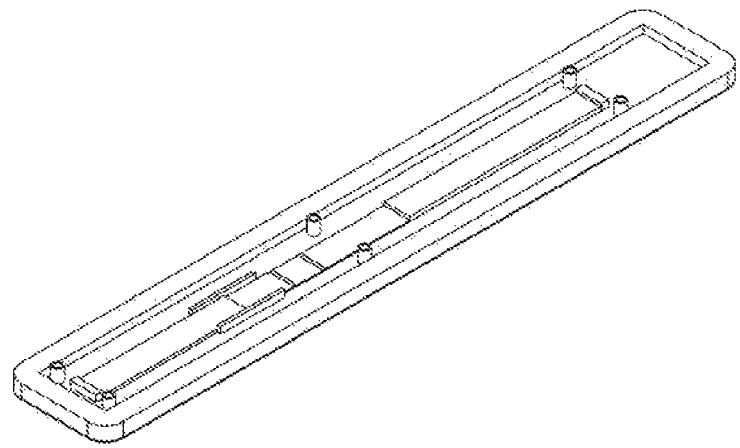
FIG. 12 illustrates a perspective section view of the assay to be analyzed 401 placed in the bottom casing 3011 of the assay holder 301.

FIG. 1 shows a perspective view of the casing of the apparatus according to the present invention, with an assay holder 301 which is slidably inserted into the internal chamber of the apparatus. FIG. 2 shows a lateral view of the apparatus, with the assay holder 301 slidably inserted. The apparatus is symmetric to its longitudinal direction. FIG. 3 shows a posterior view of the apparatus. FIG. 4 shows a top view of the apparatus, with the assay holder 301 inserted. FIG. 5 shows a bottom view of the apparatus, with the assay holder 301 slidably inserted. FIG. 6 shows a perspective section view of the apparatus's lower casing 102, with the assay holder 301 slidably inserted but the upper casing 101 is removed for illustration purpose. FIG. 7 shows a perspective section view from the bottom of the apparatus's lower casing 102 without showing the upper casing 101, and the assay holder 301 is not inserted. FIG. 8 shows a perspective section view from the bottom of the apparatus, with the assay holder 301 slidably inserted, without showing the lower casing 102 for illustration purpose. FIG. 9 shows a perspective section view from the bottom of the apparatus's internal structure, without the lower casing 102. FIG. 10 shows an exploded view of the apparatus assembly of the preferred embodiment, including the assay holder 301 as a reference. FIG. 11 shows an exploded view of the assay/holder complex 301 and 401 of the preferred embodiments. FIG. 12 shows a perspective section view of the assay to be analyzed 401 placed in the bottom casing 3011 of the assay holder 301.

The apparatus is used to analyze an assay that test a specimen of human saliva, blood, respiratory swabs, etc. The assay uses fluorescence signal to deliver the result of the test. The assay, therefore, contains a fluorescent source that interact with the target analyte present in the specimen, and is delivered to the site of interest when the assay is ready to be analyzed. The assay is analyzed by shining excitation light to the area of interest. If fluorescent source is present, the excitation light activates the fluorescent source and induces fluorescent emission, namely fluorescent signal. The apparatus also includes an excitation light source for generating an excitation light for exciting said fluorescent source of said target assay to generate said fluorescent light, a component for accurately transmitting the excitation light and the fluorescent light with less noise or reflection, a component for consistent detecting of the fluorescent source by bare eyes with minimal health risks, and a user control system that requires minimal training. Here, the component for accurately transmitting the excitation light means apparatus design, electronics, optics, or spatial arrangements that impact direction, intensity, spread, or frequency of light, or noise-to-signal ratio of the fluorescent signal, or temporal stability of light emission. For example, and it can be the arrangement of directly placing excitation light source facing the site of interest, or it could be optics that focus excitation light on the site of interest. The component for consistent and safe detecting of the fluorescent source means apparatus design, gadgets, electronics, or programs that limits user's variability in terms of shaking, timing, angle, distance, directions, or apparatus design, gadgets, electronics, programs and optics that prevent overheating or operator's harmful exposure to lights. For example, it could be automated program that turns off the excitation light source- which usually covers ultraviolet spectrum—after an interval of time. The user control system includes an interface that the user can physically interact with to change the parameters or functioning status of the apparatus. For example, it could be a button, a knob, a screen, or it could be a separate computer program.

For many usage scenarios like respiratory viral infection test, pregnancy test, or serological cancer screening, the assay is made of a long and narrow lateral flow test strip that takes in liquid specimen. This is especially the case for rapid or POC/OTC claim tests for timesaving and reducing required sample volume. In one preferred embodiment of the present invention, also referring to FIG. 11, the assay is a rapid COVID-19 fluorescent immunoassay 401. Although the test strip itself often contains all components needed for running valid tests, assay strips are usually enclosed in assay holders for stability considerations. FIG. 11 demonstrates an example of test strips enclosed in an assay holder that is designed more for non-professional uses. 301. The assay 401 includes a sequence of components that processes the test-ready sample, from first to contact with the specimen to the last are: Sample Pad 405, Fluorescent Microsphere Reservoir 404, Area of the interest 402, which can be further broke down into the Positive Band (T Band) 4021 and the Control band (C Band) 4022, and finally Adsorption Pad 403. All of these components are laid on a backing made of impermeable materials (e.g. PVC) and a nitrocellulose membrane for capillary action. When clinical specimens are well-prepared, such as completed dissolved in buffer or completed chemolysis, samples are added to the sample pad 405. The sample pad 405 slight adsorbs the specimen and keep the specimen inside the assay 401. The adsorbed specimen will move towards the other end due to capillary action.

As the specimen travels the assay, it encounters the fluorescent source of this assay: analyte specific fluorescent microsphere reservoir 404. The fluorescent microsphere travel along with the specimen, but when COVID-19 analyte, e.g. SARS-CoV-2 n protein or s protein, is present in the specimen, the fluorescent microsphere, or fluorophore, binds with the COVID-19 analyte by antibody labeling. As it passes through site of interest 402, COVID-19 analyte is captured by the antibodies precoated on Positive band 4021 that is specific to the COVID-19 analyte. As a result, fluorophores that attached to COVID-19 analytes are also stopped at the Positive Band 402. The aggregation of fluorophore makes it capable of emitting fluorescent signal that are observable by average user with bare eyes. Those fluorophores that are not attached or do not have COVID-19 analyte to attached to continue to travel with the rest of the specimen. These eventually reach and get stored by the Adsorption Pad 403, which prevents back-flow. The C-line 4022 works in a similar mechanism.

Although the test strip itself often contains all components needed for running valid tests, assay strips are usually enclosed for stability considerations. FIG. 11 demonstrates an example of test strips enclosed in an assay holder that is designed for non-professional uses. The assay holder 301 includes an upper casing 3011 and a bottom casing 3012. As FIG. 12 indicates, the test assay is placed in the bottom casing 3012 and secured by walls 3016. The two casings 3011 and 3012 are joined by pairs of connectors 3015 found on both pieces. There are two openings on the upper casing 3011, including an inlet 3013 where clinical specimen, such as serum or respiratory samples dissolved in transfer media, or other liquid reagents are loaded; and a view window 3014 that allows user to read fluorescent signals from site of interest 402, particularly the bands 4021 and 4022. The sample inlet 3013 is aligned with the sample pad 405. The view window 3014 is aligned with and should cover the area of interest 402 so that user may get a full view. The casing 3011 and 3012 shields components of the assay 402 that are irrelevant to result reading from the users.

The above mechanisms and arrangement of the rapid COVID-19 fluorescent immunoassay 401 and assay holder 301 is a good representation of similar tests in the industry.

In another preferred embodiment of the present invention, the apparatus further includes a semi-closed chamber defined by the upper casing 101 and the bottom casing 102, which is used as a backbone to contain all other components including the slidable assay holder 301. The casings of the chamber are made of impermeable materials that can shield the light transmission channels from suspending particles and environmental light noises.

In another preferred embodiment of the present invention, the apparatus backbone is made of a designated color, such as black or dark gray, to better contrast the signal fluorescent light.

In another preferred embodiment of the present invention, the apparatus contains a docking space 108, wherein the apparatus is designed to a shape such that the docking space 108 closely fits and stationizes the assay to be analyzed 401 or assay/holder complex 401 and 301. The apparatus further includes a plurality of anchor points, that reduces spatial variability of all other components, consequently limiting the user's variability in terms of shaking or wrong direction during reading process.

In another preferred embodiment of the present invention, the sample inlet of the assay holder 301 is intentionally left outside the apparatus's docking space 108 in order for the user to visually monitor the specimen, for situations such specimen running dry.

In another preferred embodiment of the present invention, wherein the casing of the chamber 101 and 102, is made of PVC.

In another preferred embodiment of the present invention, the light source 107 includes two UV-C LED lights with 365 nm frequency and 0.5 Watts power.

In another preferred embodiment of the present invention, the apparatus further includes a viewing window 103 and a plurality of spectral filtrations, such as colored translucent PVC films that blocks light with certain frequency. The plurality of spectral filtrations is applied either to the viewing windows 103 or the light source 107 in order to prevent coincidence of the fluorescent light and the excitation light or avoid human body's direct exposure to unnecessary and unintended lights.

In another preferred embodiment of the present invention, the excitation light source 107 is arranged to be not directly exposed or imposing any strong reflection into the user's eyes for safety and sensitivity concerns.

In another preferred embodiment of the present invention, the excitation light sources 107 are installed in an arrangement such that the excitation light primarily illuminates the site of interest 402 of the assay to be analyzed 401

In another preferred embodiment of the present invention, the site of interest of the assay to be analyzed and the excitation light source is placed at a 45 degrees angle and 10 mm distance, which results in least deflection.

In another preferred embodiment, the present invention teaches a method for operating the apparatus for assist analysis of the fluorescence source of the assay to be analyzed and the apparatus further includes a program, size and a plurality of specifications of the excitation light source, a docking space and a power button. The method includes the following steps:
  (a) Make sure the program, size and the plurality of specifications of the excitation light source matching the assay to be analyzed;
  (b) Insert the assay to be analyzed into the docking space;
  (c) Turn on the apparatus by pressing the power button;
  (d) Emit the excitation light to shine on the site of interest of the assay to be analyzed and excite the fluorescent source within the assay to be analyzed, which then emits fluorescent light as responses; and
  (e) The user observes the site of interest according to the instruction for use of the assay to be analyzed.

Referring to FIG. 10 that illustrates an exploded view of the apparatus assembly of the preferred embodiment and FIG. 11 that illustrates a component of the assay to be analyzed/holder complex. The components of the assay can be grouped into two categories: the apparatus category, and the assay category.

The apparatus category includes the casing and main components, and interface components. More particularly, the apparatus includes the following parts:
101—Upper Casing
102—Lower Casing
103—View Window
104—Insert Opening
105—Connector
106—Printed Circuit Board (lighting)
107—Excitation Light Source (light beads)
108—Main Docking Space
109—Printed Circuit Board (Control Panel)
110—Placeholder
111—Opening for the Button
112—Opening for the Charging Port
113—Docking space
And the interface includes the following:
201—Status Light
202—Button Interface
203—Charging Port
204—Chargeable Battery
205—Button Trigger There are many ways assays can be designed and used with the apparatus based on intended use. FIG. 10 and FIG. 11 illustrates one example, with a commercially common setup that uses lateral flow fluorescent immunoassay as the assay to be analyzed, including the following:
301—Assay holder
3011—Upper casing of the Assay holder (sub-component of 301)
3012—Lower casing of the Assay holder (sub-component of 301)
3013—Inlet for Sample/Buffer/Analyte Addition (sub-component of 301)
3014—View window of the Assay holder (sub-component of 301)
3015—Connectors of the Assay holder (sub-component of 301)
3016—Plate for Assay to be analyzed Placement (sub-component of 301)
3017—Cavity (sub-component of 301)
401—Assay to be analyzed (Test strip)
402—Area of Interest of the Assay to be analyzed (sub-component of 401)
4021—Control Line of the Assay to be analyzed (sub-component of 402)
4022—Diagnostic Line of the Assay to be analyzed (sub-component of 402)
403—Adsorption Pad of the Assay to be analyzed (sub-component of 401)
404—Fluorescent Microsphere Reservoir of the Assay to be analyzed (sub-component of 401)
405—Sample Pad of the Assay to be analyzed (sub-component of 401)

In terms of spatial arrangements, all essential components of the apparatus are coupled together in the space between the upper casing 101 and lower casing 102. The two casings are fixed to each other by pairs of connectors 105.

Internally, the upper and lower casing tightly connect to each other, which secures smaller components in space, including: excitation light emitter 107, printed circuit board for lights 106, and the control/power components 202, 205, 109, 204. The excitation light emitter 107 is soldered to PCB 106, forming a light/board complex. Two light/board complexes are installed on top of the edge of the lower casing 102, one on each side, with the excitation light emitter 107 facing the main docking space 108. The PCB 106 both serves to power to emitter 107 and to prevent light from reflecting into the docking space. In the preferred embodiment of this invention, the excitation light emitter 107 is positioned in 45 degrees angle with 10 mm distance to the site of interest 402. This arrangement hides the light emitter 107 from the user's eyes, but also the excitation light to fully cover the site of interest.

The control/power components are located in the posterior cavity. The button interface 202 is on the topmost layer, which is resting on top of the trigger 205. Both the button 202 and the button trigger 205 are stationed on the main control PCB 109. The cable charging port 203 is attached to the side of the main control PCB 109. The rechargeable battery 204 is stored in the lower compartment, underneath the control PCB. In some embodiments, replaceable dry batteries will be used instead of the rechargeable battery 204, and consequently the charging port 203 will be removed.

Externally, the casing has several openings for different purposes. In the front there is an entry opening for assay 104 which leads to the main docking space 108. The shape of outer casing 101 and 102, the entry opening 104, and the main docking space 108 should fit the assay holder 301, such that the area of interest 402 can be fully illuminated by the excitation light emitter 107. In the back there is an entry-port opening 112 that fits a cable charging port 203. On the top there are two large openings. One of them is the view window 103. The view window 103 is vertically above the area of interest 402 and aligning the view window of the assay holder 3014, so that users may view the area of interest 402 without distortions. The dimension of the view window 103 should be the same size as the area of interest 402; however, the view window 103 should not be too wide such that the excitation light emitters 107 are directly exposed to the user, such that the user may get a full view of the area of interest without safety concerns. The other opening is the opening for the button interface 111, which leaves space for the button set 202 & 205 and the status light 201.

In one preferred embodiment, the upper and lower casings 101, 102 were made of PVC, which is an example of impermeable materials that can shield the light transmission channels from suspending particles and environmental light noises. Further, the color of the casings 101, 102 are set to be black to better contrast the signal fluorescent light, which is conventionally light blue or green.

In one preferred embodiment, two UV-C LED lights of 365 nm frequency and 0.5 Watts power were used as excitation light emitter 107. Choice of light source could vary substantially based on use, but most commercially available fluorophores in the diagnostic fields are excited to visible level by this wavelength and power. Although not needed in most cases, spectral filtrations can be applied either to the viewing window or the light source in order to prevent coincidence of the fluorescent and excitation light, or to filter out dangerous frequencies of lights.

The electronic circuits of the invention are implanted in Printed Circuit Boards 107 & 109 for portability concerns. The electronics are powered by the rechargeable battery 204. When the user presses the button 202, the signal activates the status light 201 and excitation light emitter 107. The system turns on for 20 seconds and automatically turns off afterwards to prevent overheating and potential damage to the assay or eyes.

The above detailed description of the apparatus for consistent and accurate on-site readings of fluorescence signals is illustrative but not restrictive. Many more embodiments may be added within the limit of the scope.

Any modifications and adoptions without departing from the scope and spirit as set forth in the claims will still be within the protection of this invention.

What is claimed is:

1. An apparatus for quickly displaying coronavirus test result, with which a user directly reads a fluorescent light qualitatively instead of using electronic sensors, said fluorescent light is excited from a fluorescent source in a site of interest of a target assay, said apparatus comprising an excitation light source for generating an excitation light for exciting said fluorescent source of said target assay to generate said fluorescent light, a component for accurately transmitting said excitation light and said fluorescent light with less reflection, a component for consistent detecting of said fluorescent source by bare eyes with minimal health risks, and a user control system for turning on and turning off said excitation light source; said apparatus further comprising a viewing window and a plurality of spectral filtrations, wherein said plurality of spectral filtrations are applied either to said viewing window or said excitation light source in order to prevent coincidence of said fluorescent light and said excitation light.

* * * * *